US00PP23353P2

(12) United States Plant Patent
Kordes

(10) Patent No.: US PP23,353 P2
(45) Date of Patent: Jan. 29, 2013

(54) FLORIBUNDA ROSE PLANT NAMED 'KORFLOCI24'

(50) Latin Name: *Rosa hybrida*
Varietal Denomination: KORfloci24

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/136,072

(22) Filed: Jul. 22, 2011

(51) Int. Cl.
*A01H 5/00* (2006.01)

(52) U.S. Cl. ..... Plt./146

(58) Field of Classification Search ..... Plt./146
See application file for complete search history.

*Primary Examiner* — Annette Para

(57) ABSTRACT

A new and distinct variety of rose with novel pink flowers, and attractive foliage with very good disease resistance. It exhibits uniform growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfloci24'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 1999. The crossing was between an 'un-named seedling', and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfloci24'.

SUMMARY OF THE INVENTION

The new rose plant may be distinguished from its seed parent, an 'un-named seedling', by the following combination of characteristics:

1. The petal count of 'KORfloci24' is double, while the petal count of the seed parent is very double.
2. The disease resistance of 'KORfloci24' is very good while the disease resistance of the seed parent is excellent.

The new rose plant may be distinguished from its pollen parent, an 'un-named seedling' by the following combination of characteristics:

1. The flower size of 'KORfloci24' is medium while the flower size of the pollen parent is small.
2. The growth habit of 'KORfloci24' is compact while the growth habit of the pollen parent is very compact.

The objective of the hybridization was to create a new and distinct rose plant with unique qualities, such as:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORfloci24' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfloci24' was selected in May, 2000 from the seedling beds to be asexually propagated for further evaluation. The first asexual propagation of 'KORfloci24' was done by budding to seedling understocks in July, 2000 at the inventor's nursery in Offenseth-Sparrieshoop, Germany.

This initial and other subsequent propagations conducted in controlled environments demonstrate that 'KORfloci24' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORfloci24'.

DETAILED BOTANICAL DESCRIPTION

The following is a description of 'KORfloci24', as observed growing in June, 2011. in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORfloci10', a rose variety from the same inventor described and illustrated in U.S. Plant Pat. No. 19,495 and issued on Nov. 25, 2008 are compared to 'KORfloci24' in Chart 1.

CHART 1

| Characteristic | 'KORfloci24' | 'KORfloci10' |
|---|---|---|
| Flower Color: | Pink. | Light Yellow. |
| Flower Bud: | 15-20 mm (l) × | 32-35 mm (l) × |
| Upon opening, | 10-15 mm (w). | 25-27 mm (w). |
| Average petal count: | Approximately 28-34 petals. | Approximately 20-25 petals. |

Parents:

*Seed parent*.—An 'un-named seedling'.

*Pollen parent*.—An 'un-named seedling'.

Classification:

*Botanical classification*.—*Rosa hybrida* 'KORfloci24'.

*Commercial classification*.—Floribunda rose.

FLOWER AND FLOWER BUD

Blooming habit: Recurrent.

Flower bud:

*Size*.—Upon opening, 15-20 mm in length from base of receptacle to end of bud and 10-15 mm diameter at its widest point.

*Bud form*.—Short. Globular.

*Bud color*.—As sepals first unfold, bud color is Red Group 53D. When ¼ open, the upper surface of petals is Red-Purple Group 62A, and the lower surface is Red-Purple Group N57A. Guard Petals are Red-Purple Group 62A with areas of Red-Purple Group N57A.

*Sepals*.—Color: Upper surface Green Group 144A. Lower surface Green Group 144A. Size: Average 15 mm (l)×6 mm (w). Shape: Triangular. Weak foliaceous appendages on three of the five sepals. Sepals generally subulate. Sepal apex is generally cirrose. Apex: Pointed. Base: Flat at union with receptacle. Surface texture: Upper side: Moderately pubescent. Lower surface: Lightly pubescent. Margins: Pubescent with stipitate glands.

Receptacle:

*Surface*.—Smooth.

*Color*.—Yellow-Green Group 144A.

*Shape*.—Urn-shaped.

*Size*.—8 mm (h)×6 mm (w).

Peduncle:

*Surface*.—Funnel shaped. With stipitate glands.

*Length*.—30 to 35 mm average length.

*Diameter*.—1.5 to 2.5 mm average diameter.

*Color*.—Yellow-Green Group 144A.

*Strength*.—Moderately strong.

*Borne*.—Multiple flower buds per stem, generally 5 to 10.

*Anthocyanin*.—Greyed-Red Group 181A.

Flower bloom:

*Fragrance*.—Light.

*Duration*.—On the plant 5 days. Petals tend to remain attached at senescence.

*Size*.—Small for a floribunda rose. When open, the average flower diameter is 60-90 mm and the average flower height is 30 mm.

*Form*.—Shape of flower when viewed from the side: Upon opening, upper part: Flattened convex. Upon opening, lower part: Flat. Open flower, upper part: Flat. Open flower, lower part: Flattened convex.

Color:

*Upon opening, petals*.—Outermost petals: Outer Side: Red-Purple Group 62D. Inner Side: Red-Purple Group N57A. Innermost petals: Outer Side: Red-Purple Group 65C. Inner Side: Red-Purple Group N57A.

*Upon opening, basal petal spots*.—Basal petal spot, outermost petals: Outer Side: Yellow Group 2C. Inner Side: Yellow Group 2B. Basal petal spot, innermost petals: Outer Side: Yellow Group 2C. Inner Side: Yellow Group 2B.

*After opening, petals*.—Outermost petals: Outer Side: Red-Purple Group 65C. Inner Side: Red-Purple Group N66A. Innermost petals: Outer Side: Red-Purple Group 65D. Inner Side: Red-Purple Group N66C.

*After opening, basal petal spots*.—Basal petal spot, outermost petals: Outer Side: Yellow Group 1D. Inner Side: Yellow Group 1C. Basal petal spot, innermost petals: Outer Side: Yellow Group 1D. Inner Side: Yellow Group 1D.

General tonality: On open flower Red-Purple Group 63C. No change in the general tonality at the end of the 3$^{rd}$ day. Afterwards, general tonality is Red-Purple Group 58B, with the mid portion of the outer side of the petal being the principal contributor. Petal tonality is White Group N155C at finish.

Petals:

*Petal count*.—Double. Approximately 28-34 petals under normal conditions.

*Petal reflex*.—Petals reflex slightly.

*Petal edge*.—Entire.

*Petal shape*.—Obovate. Apex shape is round. Shape of base is deltoid.

*Petal size*.—35 mm (l)×35 mm (w).

*Thickness*.—Thick.

*Petal arrangement*.—Not formal.

Petaloids: Usually a few present.

*Petaloid count*.—Average of 0-4 per flower.

*Petaloid texture*.—Ruffled.

*Margins*.—Undulated.

*Petaloid shape*.—Apex: Obtuse. Base: Cuneate.

*Petaloid size*.—8-10 mm in (l)×3-4 mm in (w).

*Petaloid color*.—Color of inner side is Red Purple Group N66A. Color of outer side is Red-Purple Group N66A.

Reproductive organs:

*Pistils*.—Average. Approximately 65 present. Stigmas: Location: Slightly inferior in position to anthers. Color: Yellow Group 2D. Styles: Length: About 6 mm long. Color: Yellow Group 1D.

*Stamens*.—Approximately 110 on average and regularly arranged. Anthers: Size: 1 mm long, on average. Pollen: Generally present. Color: Greyed-Red Group N199D. Filaments: Color: Yellow Group 2B. Length: About 8 mm.

THE PLANT

Growth: Moderately vigorous.

Plant habit: Compact and bushy habit. When grown as a budded field grown plant, the average plant height is 75 cm and the average plant width is 40 cm.

Stems:

*Stem color*.—Young wood: Yellow-Green Group 144B. Older wood: Yellow-Green Group 144A. Stem surface: Young wood: Smooth. Older wood: Smooth.

Prickles: Present.

*Incidence*.—Approximately 5-10 per each 10 cm of stem.

*Size*.—Average length: 5 mm.

*Color*.—Immature prickles: Greyed-Purple Group 183B. Mature prickles: Greyed-Purple Group 182B. Senescing to Greyed-Orange Group 165B.

*Shape*.—Linear.

*Anthocyanin*.—Color Greyed-Purple Group 183B.

Leaves and leaflets: Normally 7 leaflets on normal leaves in middle of the stem.

*Leaf size*.—40 mm (l)×80 mm (w).

*Abundance*.—Average.

*Texture*.—Thin. Upper side of leaflet: Semi-Glossy. Under side of leaflet: Matte.

*Color, mature foliage*.—Upper Leaf Surface: Green Group 137A. Lower Leaf Surface: Green Group 146B.

*Color, juvenile foliage*.—Upper Leaf Surface: Green Group 139A. Lower Leaf Surface: Green Group 146B.

*Anthocyanin intonation*.—Present. Intonations present on juvenile leaf margins, and leaf undersides. Color is Greyed-Purple Group 183A.

Stipules:

*Size*.—23 mm long. 10 mm between the tips of the stipules. Main body of stipule 6 mm in width.

*Stipule color*.—Green Group 146B.

*Anthocyanin*.—Greyed-Red Group 182B.

*Stipitate glands*.—Present.

*Margins*.—With stipitate glands.

*Shape*.—Apex: Apiculate. Base: Winged.

Petiole:

*Length*.—About 20 mm.

*Diameter*.—About 2 mm.

*Petiole color*.—Yellow-Green Group 144A.

*Underneath*.—Smooth.

*Margins*.—Normally smooth and without stipitate glands.

*Anthocyanin*.—Greyed-Red Group 183A.

*Prickles*.—Lacking.

Petiole rachis:

*Length*.—40-50 mm on average.

*Diameter*.—1-2 mm on average.

*Color*.—Yellow-Green Group 144A.

*Underneath*.—Mostly smooth with a few prickles present.

*Margins*.—Prominent stipitate glands.

*Anthocyanin*.—Present on young foliage.

*Prickles*.—Present 3-5 per rachis.

*Stipitate glands*.—Present on margins.

Leaflets:

*Size*.—Average size of the terminal leaflet is 30 mm (l)×25 mm (w).

*Shape*.—Ovate. Base: Ovate. Apex: Micronate.

*Margins*.—Finely serrated.

*Texture*.—Thin.

Hips/seed formation: None observed.

Winter hardiness: To date, the variety has been grown successfully in Zone 5.

Disease resistance: Above average resistance to powdery mildew (*Sphaerotheca pannosa*), blackspot (*Diplocarpon rosae*), and rust (*Phragmidium* sp.) diseases under normal growing conditions.

I claim:

1. A new and distinct variety of rose plant, as described and illustrated herein.

* * * * *

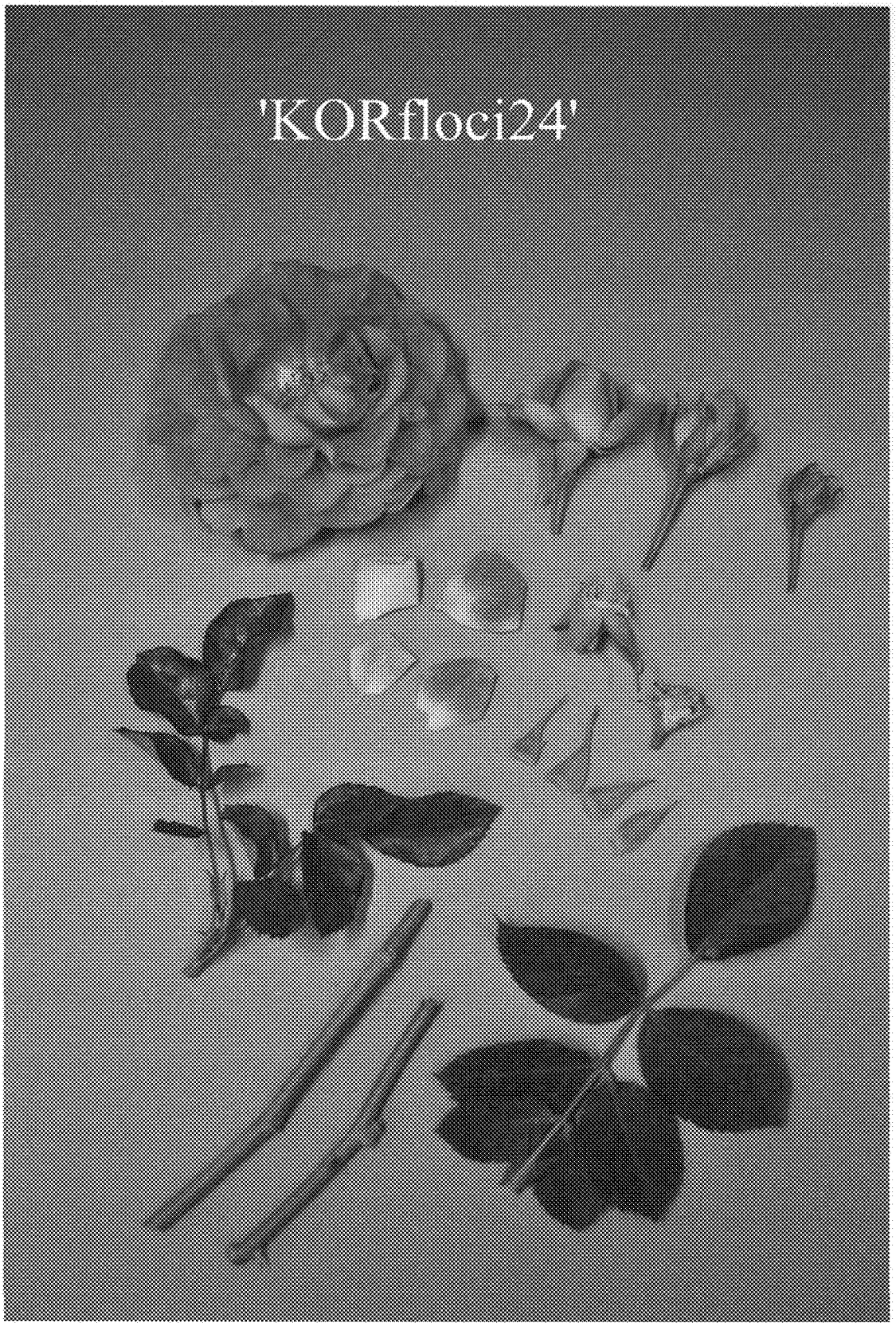
'KORfloci24'